(12) United States Patent
Arora

(10) Patent No.: US 11,779,523 B2
(45) Date of Patent: *Oct. 10, 2023

(54) SYSTEMS, METHODS AND APPARATUS FOR SUBSTANCE DEPENDENCE CESSATION MANAGEMENT

(71) Applicant: Robin Arora, Huntington, WV (US)

(72) Inventor: Robin Arora, Huntington, WV (US)

( * ) Notice: Subject to any disclaimer, the term of this patent is extended or adjusted under 35 U.S.C. 154(b) by 76 days.

This patent is subject to a terminal disclaimer.

(21) Appl. No.: 17/315,158

(22) Filed: May 7, 2021

(65) Prior Publication Data

US 2021/0259923 A1    Aug. 26, 2021

Related U.S. Application Data

(63) Continuation of application No. 16/276,524, filed on Feb. 14, 2019, now Pat. No. 11,007,121.

(60) Provisional application No. 62/631,025, filed on Feb. 15, 2018.

(51) Int. Cl.
    *A61J 7/04*             (2006.01)
    *A61J 7/00*             (2006.01)
    *G16H 20/13*          (2018.01)

(52) U.S. Cl.
    CPC ........... *A61J 7/0481* (2013.01); *A61J 7/0076* (2013.01); *A61J 7/0418* (2015.05); *G16H 20/13* (2018.01)

(58) Field of Classification Search
    CPC ...... A61J 7/0481; A61J 7/0418; A61J 7/0076; G16H 20/13
    See application file for complete search history.

(56) References Cited

U.S. PATENT DOCUMENTS

| | | | |
|---|---|---|---|
| 8,452,446 B1* | 5/2013 | Madris | A61J 7/0084 |
| | | | 221/133 |
| 10,692,052 B2* | 6/2020 | Fernando | A24F 40/80 |
| 10,939,878 B2* | 3/2021 | Kiani | A61B 5/0022 |
| 11,007,121 B2* | 5/2021 | Arora | A61J 7/0481 |
| 2006/0064037 A1* | 3/2006 | Shalon | A61B 5/0031 |
| | | | 128/903 |
| 2010/0242975 A1* | 9/2010 | Hearn | F17C 5/06 |
| | | | 131/273 |
| 2010/0270257 A1* | 10/2010 | Wachman | G06Q 10/10 |
| | | | 215/228 |
| 2011/0172812 A1* | 7/2011 | Joslyn | A61J 7/0409 |
| | | | 340/815.4 |
| 2015/0181945 A1* | 7/2015 | Tremblay | A24F 40/60 |
| | | | 131/328 |
| 2015/0287007 A1* | 10/2015 | Suralikal | G07F 9/001 |
| | | | 700/237 |

(Continued)

*Primary Examiner* — Michael Collins
(74) *Attorney, Agent, or Firm* — Mahesh Law Group PC; Kumar Maheshwari

(57) ABSTRACT

Systems, methods and apparatus for substance dependence cessation management are described. The system involves an electronic mobile device, a communication network and a substance packet holder adapted with a substance packet dispenser, the substance packet holder connected to the electronic mobile device through the communication network. The system being capable of collecting user related information of a user for activating for an algorithm on the electronic mobile device based on the user related information, defining a plan for the cessation of substance dependence and capable of controlling a dispensing of a substance packet from the substance packet dispenser for the user.

20 Claims, 16 Drawing Sheets

(56) References Cited

U.S. PATENT DOCUMENTS

2017/0098056 A1\* 4/2017 Reddy ................... G16H 20/13
2017/0372018 A1\* 12/2017 Rosenblatt ........... A61B 5/4824

\* cited by examiner

SYSTEMS, METHODS AND APPARATUS FOR SUBSTANCE DEPENDENCE CESSATION MANAGEMENT

PRIORITY CLAIM TO RELATED APPLICATIONS

This application is a continuation application of U.S. patent application Ser. No. 16/276,524, entitled as "SYSTEMS, METHODS AND APPARATUS FOR SUBSTANCE DEPENDENCE CESSATION MANAGEMENT", filed Feb. 14, 2019, which claimed benefit of U.S. Provisional Patent Application No. 62/631,025, entitled as "Systems, Methods and Apparatus for Substance Dependence Cessation Management", filed on Feb. 15, 2018, the disclosures of which are incorporated by reference in their entirety.

FIELD

The present disclosure generally relates to systems, methods and apparatus for substance dependence cessation management.

BACKGROUND

Substance abuse affects a larger portion of human population in the world. In terms of people who are affected directly such as families of abusers and indirectly include those injured or killed by intoxicated abusers, an additional portion of the population are affected. A general survey indicates that "Substance dependence and substance addiction", can be diagnosed with physiological impact, evidence of tolerance or withdrawal, or without physiological impact. For exemplary purposes, the various kinds of substance involved in Substance dependencies and addictions include, alcohols, opioids, sedatives, hypnotics, anxiolytics, benzodiapenes, barbiturates, hallucinogens, inhalants, polysubstance, phencyclidines nicotine and nicotine-based substances.

A state of substance tolerance is reached when a physical habituation to a substance is gained by frequent use of the substance, such that in consequent consumptions, higher doses of the substance are required to achieve the same effect. Substance withdrawal symptoms are a cluster of symptoms that occur when a user stops using a particular addictive substance following heavy and prolonged use. People who experience withdrawal symptoms often return to the substance usage to relieve the discomfort associated with withdrawal symptoms, causing a relapse.

The words substance dependence and substance addiction are often used interchangeably, but there are important differences between the two. Dependence specifically refers to a physical condition in which the body has adapted to the presence of a substance in the body. Although dependence is often a part of addiction, non-addictive substances can also produce dependence in patients. A prime example is prednisone, a synthetic form of the steroid hormone cortisol that is used to treat asthma, allergic reactions.

Substance dependence and substance addiction are treatable conditions. Methods and systems for reducing the dosage of the patient from the substance slowly may be beneficial.

SUMMARY

Embodiments are directed to a gradual reduction of dose of a substance monitored with a customized algorithm to assist in substance dependence cessation or substance addiction cessation without any or at least reduced withdrawal symptoms.

In an embodiment of the present inventive subject matter, a system for substance dependence cessation management, is described involving an electronic mobile device, a communication network and a substance packet holder adapted with a substance packet dispenser, connected to the electronic mobile device through the communication network. The system is capable of collecting user related information required for an algorithm. The system adapted to activate an algorithm on the connected electronic device based on user related information and defining a plan for the cessation of substance dependence and capable of controlling the dispensing of substance packets from the substance dispenser. The system capable of identifying a substance dispenser proximate to the user for dispensing the substance packets at scheduled times. The system capable of rewarding the user for adhering to the number of substance packets dispensed by the algorithm-controlled substance packet dispenser. The system capable of dispensing substance packet only at the dispenser nearest to the user. The system capable of ensuring the substance packets are dispensed only at a single dispenser at a given timeframe.

In another embodiment of the present inventive subject matter, a method for substance dependence cessation management is described. The method involves, registering a user for substance dependence cessation management, collecting user's substance dependence related information, saving user's substance dependence related information and generating a substance dependence cessation plan for the user. The method further providing instructions to the user regarding a number of substance packets to be loaded into a substance dispenser and controlling a number of substance packets dispensed from a substance packet holder, to the user at a given time frame.

In yet another embodiment of the present inventive subject matter, an apparatus for substance dependence cessation management is described. The apparatus involves a substance packet holder chamber, the substance packet holder chamber adapted to hold one or more substance packets and a substance packet dispenser embedded in the substance packet holder chamber capable of being controlled by a software program to dispense a particular number of substance packet at a specific time.

BRIEF DESCRIPTION OF THE DRAWINGS

Many aspects of the present invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF DISCLOSURE

Figure 1:
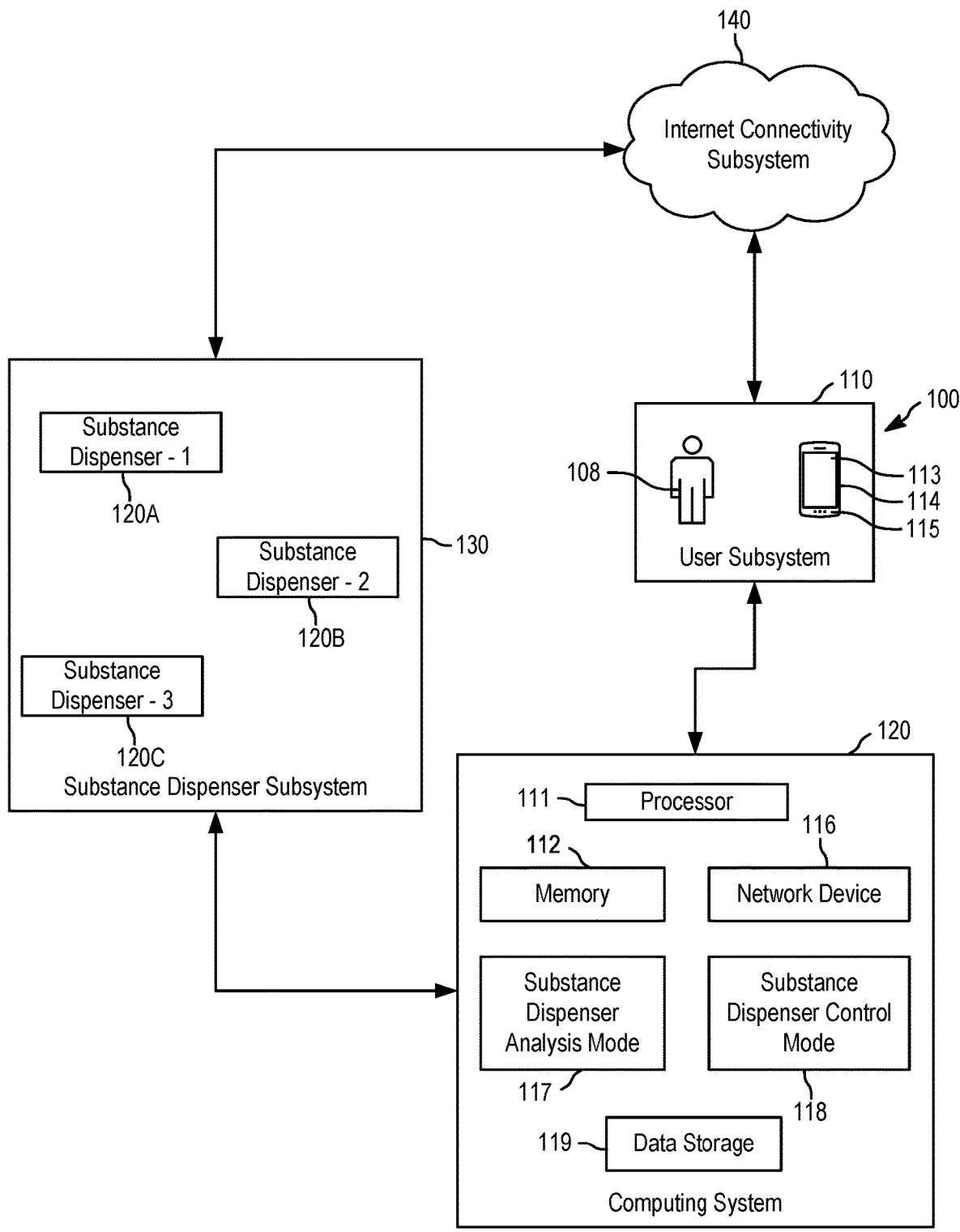
FIG. 1 illustrates a system for substance dependence cessation management.

Before turning to the figures, which illustrate the exemplary embodiments in detail, it should be understood that the application is not limited to the details or methodology set forth in the description or illustrated in the figures. It should also be understood that the terminology is for purpose of description only and should not be regarded as limiting.

Embodiments of the present disclosure include a user customized substance dependence cessation (SDC) planning, administrating and executing system that may utilize a mobile device or other digital device, to collect user information and feed the collected information to the SDC planning system for generating a workable SDC plan.

Referring generally to the figures, embodiments of the systems and methods described herein are directed to assisting user in cessation of substance dependence or substance addiction. For exemplary purposes, the different embodiments describe, systems, methods and apparatus for cessation of substance dependence in detail throughout the disclosure. The described embodiments for cessation of substance dependence can be tailored for usage for cessation of substance addiction too. Embodiments are directed towards a user customized plan generated by the substance dependence cessation system for achieving substance dependence cessation in a healthy way with minimum or no withdrawal symptoms for a user. Embodiments are directed to a software application platform combining the unique features of a substance dispensing analysis module and a substance dispensing module which work conjointly to put together the substance dependence cessation plan as described above.

The system has a digital user interface or application which may be downloaded on any user possessed digital device through the internet. One purpose of the application is to register user for SDC plan, create unique user ID, collect user specific information and communicate the information to the SDC planner for generating user customized SDC plan. Cloud or premise-based servers may be configured to use user's basic information, including user profile history and send the information to a data storage to archive that approved user details on system servers connected to SDC platforms and user associated data bases.

As described, the system comprises several components arranged in various configuration to maximize efficiency of communication between the components. The system is designed to be used by one or more users according to the needs of users from a single geolocation or from different geolocations and yet being connected by a user network generated by the SDC computing subsystem. The system includes a web-based SDC software application, which is accessible through a variety of computing devices, including but not limited to such as desktop computers equipped with a web browser, as well through native mobile applications installed on mobile computing devices such as smartphones and tablets. A cloud-based infrastructure comprising a server and SDC database configured to receive information from user and user devices via the Internet, by way of cellular networks, wired and wireless routers, and local area networks (LANs) of varying size and configuration. On the other hand, the present invention provides a user customized plan for substance dependence cessation by gradually reducing the dose of the substance over a user appropriate period of time.

Embodiments of the present disclosure are directed to interact as an integrated whole as means of planning, administering and executing and providing a user feasible substance dependence cessation plan, all the while automating and networking many traditional manual processes and collecting and storing valuable user specific information for later queries and retrieval for operational efficiency analysis.

As described, the present system, method and apparatus is delineated specifically for use within a substance abuse cessation environment, more specifically for a substance dependence or a substance addiction cessation management for users, but may also be configured and scaled to function within larger, more user-dense environments with multiple substance dependence or addictions, managed by a single SDC system.

Referring to FIG. 1, FIG. 1 depicts the different key components of a system 100 for SDC management. The system 100 further includes, a user subsystem 110, a computing subsystem 120, a substance dispenser subsystem 130 and an internet connectivity subsystem 140. All these subsystems conjointly work towards delivering a substance dependence cessation plan for benefitting an interested user.

A user subsystem 110 includes one or more users 108, with a mobile computing device 113 having a display 114 and software application 115. A user 108 inputs his/her information through a display 114 of a mobile computing device 113 upon prompting by an SDC application or SDC app on their mobile computing device 113. The mobile computing device 113, a smart phone or another mobile device, would require an internet access to download the software applications SDC app 115. The compatibility of a software app with the device is vital for the good performance of the app on the device. The software app, SDC app 115, disclosed in this invention is compatible with most operating systems, Android, Apple, Microsoft, Amazon, and BlackBerry mobile operating systems, thus making it easily accessible by wide variety of user. A network communication device 116 is a hardware device capable of transmitting an analog or digital signal with other computing devices and the computing subsystem 120. One or more users 108 with one or more mobile computing devices 113 are connected into a meshed network with the computing subsystem 120. The network communication device 116 may include, a computer Modem, a network interface card (NIC), Wi-Fi devices, an access point, Bluetooth devices, Infrared devices, Network card (using Ethernet), Smartphone and Wi-Fi devices (using a Wi-Fi router). For example, but not limited to, a Bluetooth RF technology based device may be implemented that operates at 2.4 GHz, has an effective range of 32-feet, and has a transfer rate of 1 Mbps and throughput of 721 Kbps to connect a user mobile computing device 113 with the computing subsystem 120.

Specifically, FIG. 1 depicts a system for registering one or more user 108, collecting user specific information, like personal information, location information, substance usage profile by users 108 and creating unique user profile data for generation of user customized SDC plan. The user 108 is provided with the comfort of providing their information from their mobile computing device 113, without the need to physically travel to a substance abuse help centers for treatment purposes. Upon automatic prompting on their mobile computing device 113, the user 108 provide their substance use profile, privately and securely to a data storage server 119 via a software SDC application or SDC app 115 on their mobile computing device 113 e.g. smart phone, tablet or etc.

Additionally, FIG. 1 depicts a system 100 for identifying and tracking the location of a user at different times of a day by location-based search capability of the internet connectivity subsystem 140, so as to efficiently optimize and execute the SDC plan by a computing subsystem 120, with a substance dispenser subsystem 130, which is in near proximity to the user. The "substance" as described throughout the present disclosure includes alcohol, opioids, cocaine caffeine, nicotine and any other substance dependable or addictive substance in the form a substance packet. The term substance packet includes, an alcohol bottle, a drug substance in a capsule, drug substance in a casing, drug substance in a wrapper, drug substance in a container, drug substance in an envelope, drug substance in an edible tablet or a drug substance in a can.

A computing subsystem 120 includes a central processing unit or a processor 111, an exemplary processor, such as, but not limited to, a Pentium processor or an Athlon processor or a Phenom Processor or a Duron processor or a Core Series Processor may be implemented to receive instructions from a memory 112. In the alternative, a multi-core processor may be implemented, which means that system contains two or more processors for enhanced performance, reduced power consumption and more efficient simultaneous processing of multiple tasks. Principal components of a processor 111 include an arithmetic logic unit, a processor registers unit and a control unit. The arithmetic logic unit mainly performs arithmetic and logic operations for generation of the SDC plan. The processor registers supply all the required operands to the Arithmetic logic unit and store the results of arithmetic logic unit operations. The control unit controls the data fetching from memory 112 and execution of instructions by directing the coordinated operations of the arithmetic logic unit, processor registers, control unit and other components. The processor 111 has relatively some memory storage and has may have only enough memory to hold a few instructions of a program and the data they process with the arithmetic logic unit. The results achieved by the arithmetic logic unit in the form of data sets are held in memory external to the processor 111, as a main memory, and a secondary memory. The main memory also called volatile, loses its information when power is removed. Secondary memory is usually nonvolatile because it retains its information when power is removed. The incoming data is initially stored in random access memory. The processor then stores pieces of data it will need to access, in a priority of use order in a cache, and maintains certain special instructions in the register for retrieving the data accordingly.

The computing subsystem 120 controls and supervises the operation of the substance dispensing subsystem 130 through the SDC app 115. The two main component modules playing a vital software role in planning, administering and executing a user customized SDC plan are substance dispensing analysis module 117 and substance dispensing control module 118. The substance dispensing analysis module reviews and analyses the data collected by the processor 111, inputted by the user 108 through his/her mobile computing device 113 via the SDC app. Based on the data collected for the user profile, substance dispensing analysis module 117 analyses a general health of the user, the commitment promised by the user, the user selected method for cessation, a cold-turkey cessation, a fast rate cessation, a medium rate cessation or a slow rate cessation. The user 108 is asked to answer one or more questions before generating a user customized SDC plan. Substance dispensing analysis module 117 interacts with the processor 111 to lay out the structure for the SDC plan. An SDC algorithm is defined, which is an effective method that can be expressed based on user profile data and in a well-defined formal language for calculating a SDC plan. Starting from an initial state and initial input by the user 108, the SDC algorithm instructions describe a computation that, when executed, proceeds through a finite number of well-defined successive states, eventually producing a user customized SDC plan and terminating at a final ending state. The arithmetic logic unit of the processor 111 functions as a combination logic circuit, wherein the output will change in response to asynchronous changes in input based on the collected user profile records. The different operations, which may be executed to lay out the SDC plan includes, arithmetic operations, bitwise logical operations and bit shift operations. Operations like add, subtract, increment and decrement are a few examples of arithmetic operations supported by the processor. Bitwise logical operations supported by the Arithmetic logic unit include AND, OR, Exclusive-OR. Bit shift operations like arithmetic shift, logical shift, rotate and rotate through carry operations help in transforming the data collected by the user profile to be converted to meaningful SDC plan attributes.

The substance dispensing control module 118, plays a major role in executing the SDC plan generated by the computing subsystem 120 with the substance dispensing subsystem 130. The substance dispensing control module 118 mainly communicates with the Network communication device 116 to lay out a plan of the location detail of the different subcomponents of the substance dispenser subsystem 130. The rate at which a substance is dispensed at each of the substance dispensing subsystem 130 is also controlled by the substance dispensing control module 118. The main function of the substance dispensing control module 118 is to monitor and make sure a substance is dispensed at one and only one substance dispensing subsystem 130 in near proximity to the user at a given time interval, so as to avoid excessive dispensing of substance or dispensing of substances at one or more locations at the same given time interval.

The data storage 119 of the computing system handles all the data necessary for planning executing and post execution detailing of the SDC plan for one or more users at various locations. The data representing user profile information, user customized SDC plan attributes generated for one or more users in the form of numbers, lab results, profile pictures, audio, and nearly any other form of information is converted into a string of bits, or binary digits, each of which has a value of 1 or 0 and stored as a byte, equal to 8 bits. This form stored information can be communicated between one or more computer or user mobile computing device 113, whose storage space is large enough to accommodate the binary representation of data. Many standards exist for encoding including, character encodings like ASCII, image encodings like JPEG, video encodings like MPEG-4. By adding bits to each encoded unit, redundancy allows the computer to both detect errors in coded data and correct them based on mathematical algorithms. The cyclic redundancy check method is typically used in communications and storage for error detection. For security reasons data may be kept encrypted in data storage 119 to prevent the possibility of unauthorized information reconstruction from chunks of storage snapshots. The data storage 119 forms the base for data sharing with external entities including clinical professionals or even other users. The data storage 119 provides the information necessary for publishing success stories of successful cessation of substance dependence by users at their own rates, which would serve as inspirational quotes and records for new users.

A substance dispensing subsystem 130 comprises of one or more substance dispensers associated with a user in a multiple user network. The operational features of the substance dispensing subsystem are completely controlled by the computing subsystem 120 according to the generated user customized SDC plan. A single user may possess one or more substance dispensers, substance dispenser-1 130A, substance dispenser-2 130B and substance dispenser-3 130C connected to his/her SDC plan to dispense the substance at different intervals of the day. For example, the different locations for the substance dispensers 130 A/B/C include, home, office, car, fitness center etc. Each of the substances dispenser is identifiable by its unique identifiers assigned by the computing subsystem 120. Each of the substance dispensers can be embedded with location revealing sensors like Bluetooth tooth beacons, to estimate the proximity of a substance dispenser to a user at a given interval of time.

Figure 2:
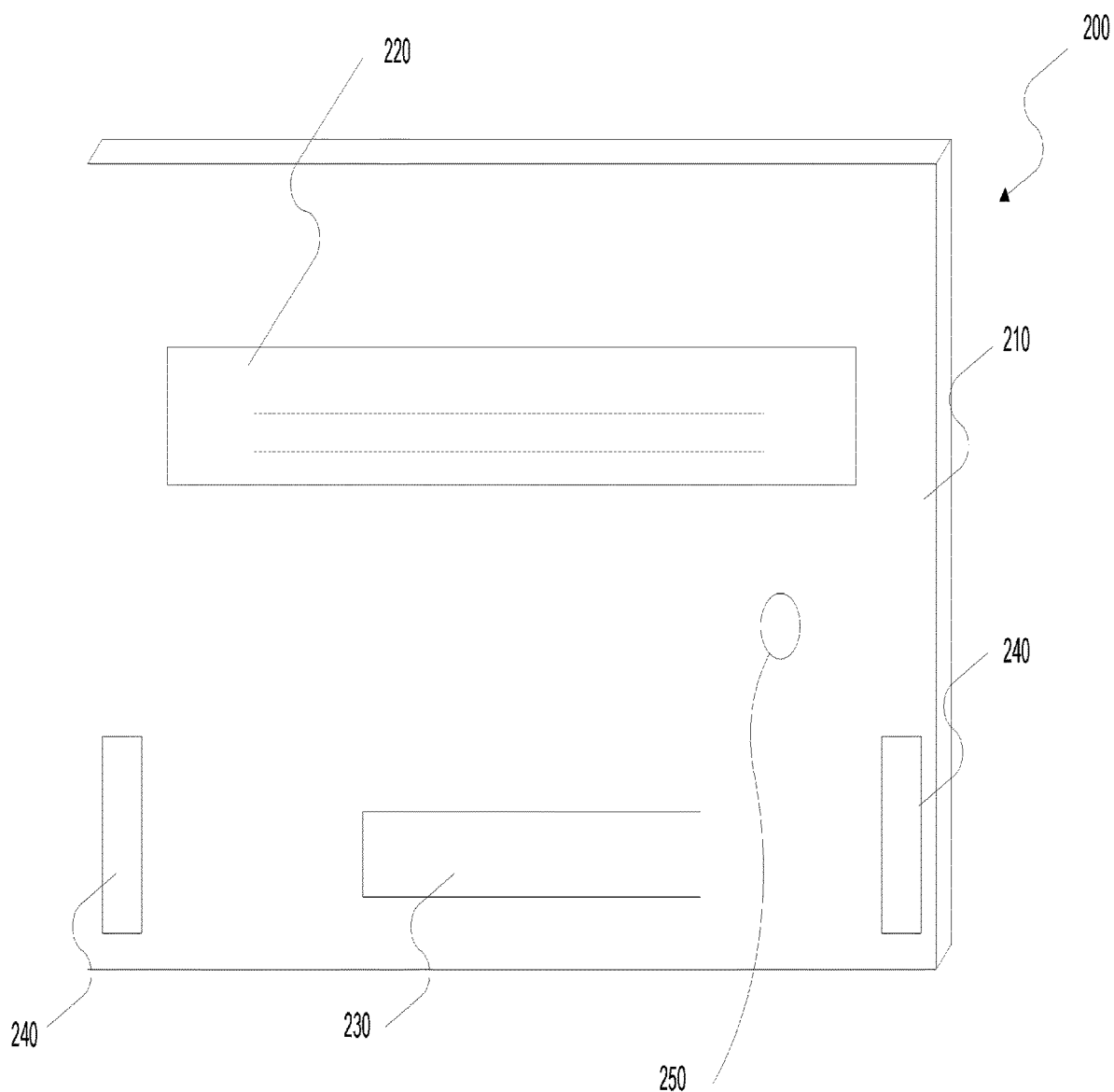
FIG. 2 illustrates a schematic diagram of a substance dependence cessation apparatus.

A representative example of a substance dispenser apparatus 200 is as shown in FIG. 2. The substance dispenser apparatus 200, is configured to execute the instructions defined by the computing subsystem 120. The substance dispenser apparatus 200, comprises a chamber 210 for holding one or more substance packets, embedded with a sensor to determine the number of substance packets in the chamber, to be displayed on a substance dispenser display 220. The information regarding the number of substance packets is communicated back to the computing subsystem 120. The chamber has a dispensing outlet 230 through which the substance is dispensed according to the SDC planner. The opening and closing of the chamber for loading the substance packets is controlled by a computing subsystem. Thus, making sure that the substance packet is available for the user only according to the SDC plan and not at the wish of the user. The substance dispenser displays 220 is also used for displaying greeting and encouraging messages to the user and to throughput any other important messages to the user. The apparatus may also be equipped with a pair of speaker 240 to play any important greeting audio clips or encouraging words to the user by the computing subsystem 120. The substance dispenser apparatus 200 can also be equipped with a craving button 250, which can be used to communicate the craving feeling of the user to the computing subsystem. In an alternative embodiment, the user 108 may communicate the craving feeling to the computing subsystem 120 through the SDC app 115 on the user mobile communicating device 113. As soon as a communication is received regarding the craving feeling of the user, either by the activation of the craving button or through the SDC app the computing subsystem accommodates the user request and manipulates to the SDC to satisfy the user's craving feeling. As research has shown that by meeting the craving feature there is greater probability that the user will stick back with his SDC plan rather than trying to circumvent the craving feeling.

In some embodiments the power source for the substance dispenser apparatus 200, comprises a disposable battery or a rechargeable battery, wherein the rechargeable battery is configured with an optional battery charging mechanism, like an external charging station or a solar cell powered battery charger. In an alternative embodiment, the substance dispenser apparatus 200 can be connected by a hard-wired circuit to a power source with a plug point.

In an exemplary embodiment, a mechanical dispensing coil may be used for dispensing the substance packets from the substances dispenser apparatus 200. In an alternative, an electronically activated motor may be implemented, which spins and generates a vibrational motion in a spiraled substance holder inside the substance dispenser. When the computing subsystem 120 sends an instruction to the substance dispenser apparatus 200 to dispense a substance packet, the motor is electronically activated, leading to a vibrational motion of the substance packet holder, thus pushing the substance packets forward. Due to the vibrational motion, when the substance packet reaches the end of the substance packet holder, it simply falls due to gravity into the dispensing outlet 230 at the bottom of the substance dispenser apparatus 200.

The internet connectivity subsystem 140 is responsible for the information flow between the one or more user 108 of the user subsystem 110, computing subsystem 120 and the substance dispenser subsystem 130. The different types of internet connectivity which can be used to support the embodiments described in this disclosure include, Dial-Up, DSL, Wi-Fi, or Cellular connectivity. The internet connectivity subsystem 140 helps in finding the location details of the user by tracking the mobile communication device of the user. The location details of the substance dispenser subsystems in near proximity to the user is estimated by the information given out by the embedded location beacons to execute the SDC plan with the appropriate substance dispenser subsystem.

Figure 3:
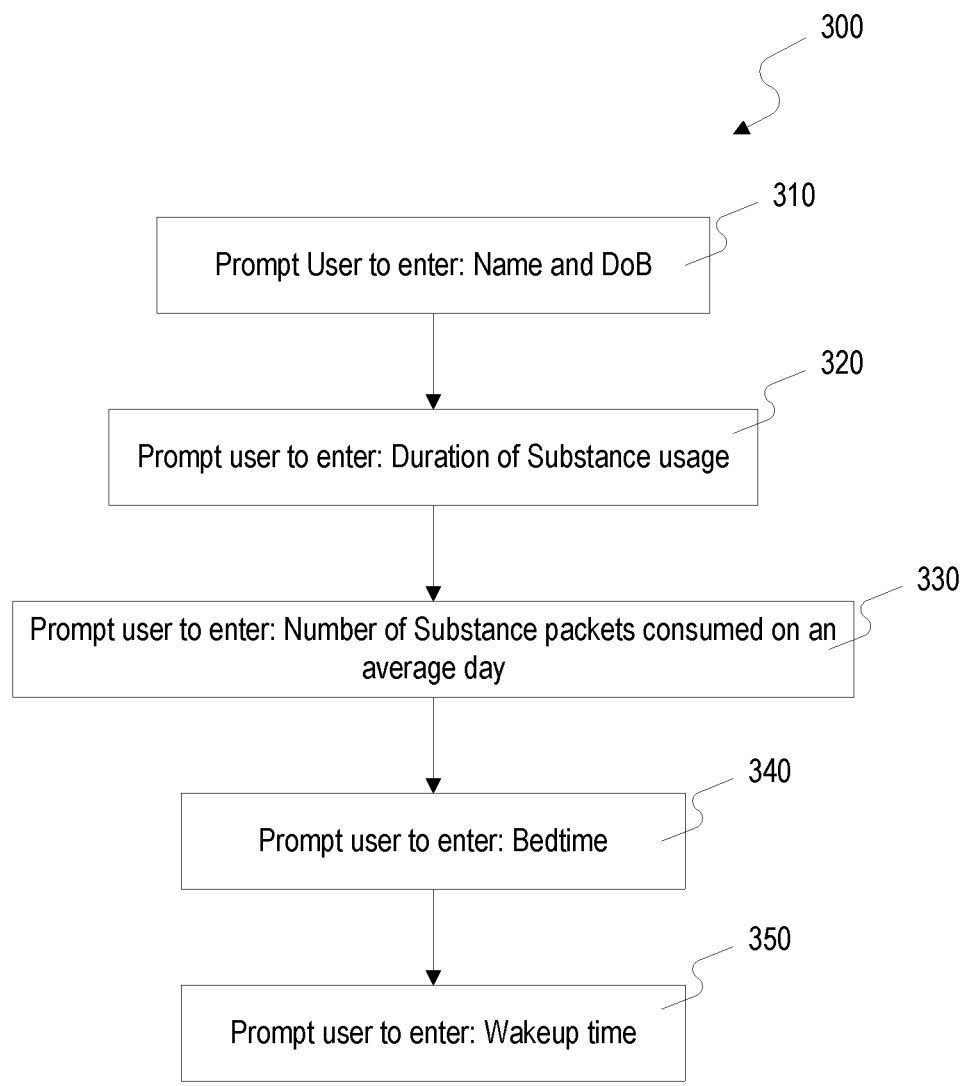
FIG. 3 illustrates a flow chart for user information collection.

Referring to FIG. 3, FIG. 3 describes a process 300 that may be used to collect substance use (e.g., substance may be narcotics, nicotine, demerol, cigarettes, tobacco, sweets, fatty foods) related data of one or more users 108. The display 114 generates a screen that prompts the user for an input regarding user profile information from the user 108 on his/her mobile computing device 113. Upon receiving the information, the user, the user profile information is stored by the processor in the data storage 119. Initially, at step 310, a user is prompted to enter his/her name and date of birth. The computing subsystem upon receiving the user name and date of birth information, registers the user as a new user and creates a unique user identification to be used by the SDC app for generating the user customized SDC plan. At step 320, the user is prompted to enter the duration of substance dependence or how many years the user has been dependent on the substance. The information regarding the substance dependence duration helps in defining the level of the substance dependence as light, medium or severe. At step 330, a user is prompted to provide information regarding the number of substance packets consumed on an average day. The information regarding the frequency of the substance packet consumption helps in defining severity of the dependence. At steps 340 and 350, the user's bed time and wake up time is collected to calculate an average wake time of a patient, which would be the most probable duration for the substance consumption in a day. After collecting the information for the user 108 regarding the user profile information, the substance dispenser analysis module of the computing subsystem 120, analysis the user data, to sketch a profile for the user regarding the substance he/she is dependent on and the severity of the dependence and the general health of the user and feeds all these information to an SDC algorithm to generate the user customized SDC plan.

Figure 4:
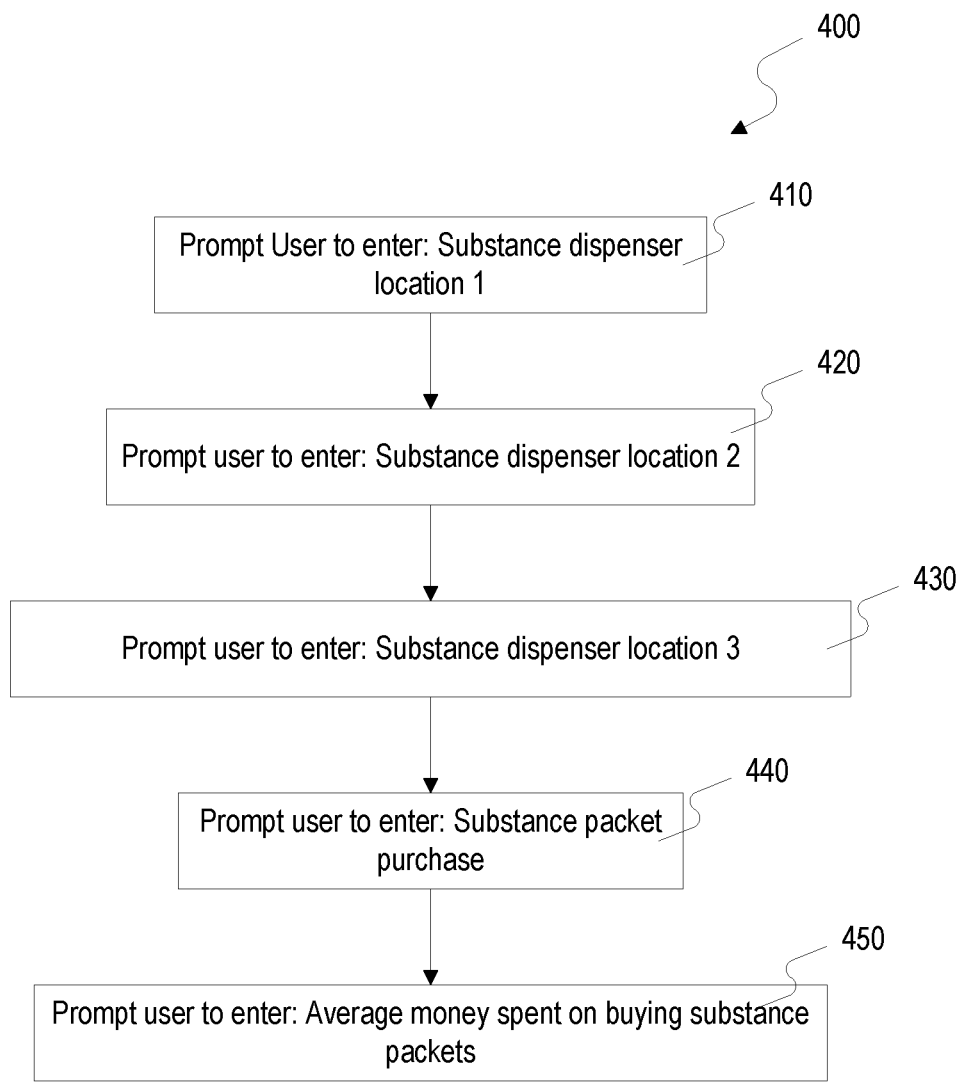
FIG. 4 illustrates a flow chart for user information collection.

Referring to FIG. 4, FIG. 4 describes a process 400 that may be used to collect substance usage locations related data of one or more users 108. The display 114 generates a screen that prompts the user for an input regarding substance usage location information from the user 108 on his/her mobile computing device 113. Upon receiving the information from the user, the user profile information is stored by the processor in the data storage 119 and communicated to the substance dispenser analysis module 117 and substance dispenser control module 118. The SDC plan generated for the user is built upon the proximity of the substance usage locations to the user at different time intervals of the day. At step 410, a user is prompted to enter substance usage location 1. For example, the substance usage location 1 may include a residence of the user. At step 420, a user is prompted to enter substance usage location 2. For example, the substance usage location 2 may include a vehicle the user uses to travel to his/her office. At step 430, a user is prompted to enter substance usage location 3. For example, the substance usage location 3 may include an office of the user. At step 440, a user is prompted to enter location of substance purchase. The computing subsystem 120 in conjunction with the internet connectivity subsystem 140 subsystem estimates the number of trips taken to the substance purchase store. At step 450, a user is prompted to enter the average money spent on buying substance packets. In alternative embodiments, the user's bank cards like credit cards, debit cards can be tracked by the internet connectivity subsystem to track the expenditure on substance packets and to estimate the user's consumption of the purchased substance packets. The substance usage location, 1/2/3 includes, but not limited to, home, office, car.

Figure 5:
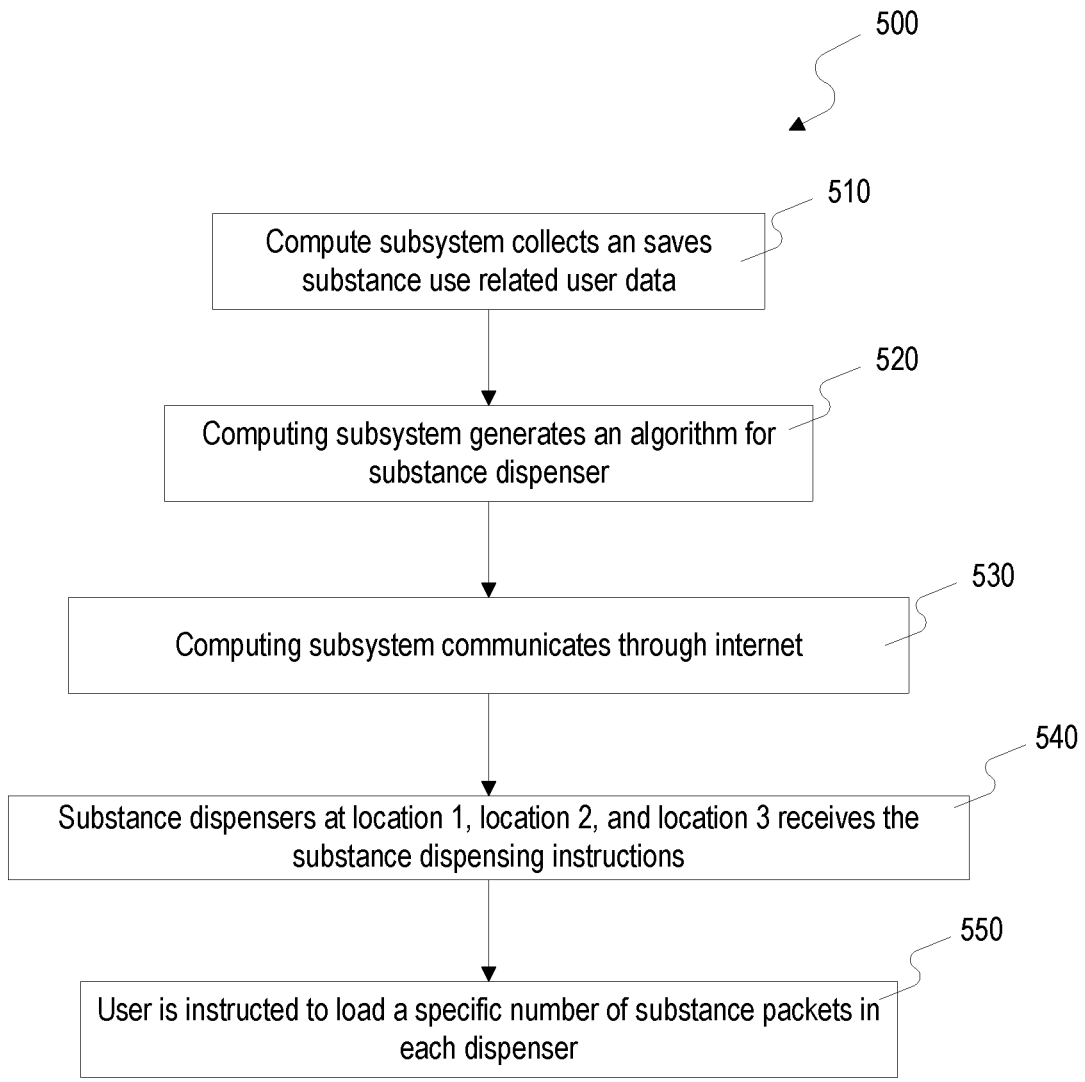
FIG. 5 illustrates a flow chart of operation of substance cessation management system.

In a non-limiting embodiment, FIG. 5 describes a flowchart 500, for an operational or executional structure for the substance dependence cessation management. At step 510, the computing subsystem 120 collects and saves substance dependence related user data and the substance dispenser analysis module 117 prepares all the necessary requisites for a user customized SDC algorithm. The SDC algorithm is mainly dependent on the input information from user regarding the substance dependence history. At step 520, computing subsystem 120 generates a workable SDC plan for the user based on user details provided by user in steps 210-250 and 310-350 described above and executes the plan through the substance dispenser control module 118. At step 530, the computing subsystem communicates the work plan through the internet connectivity subsystem 140 and the different substance dispensers are loaded with substance packet dispensing instructions. At step 550, user is instructed to load a specific number of substance packets in the substance dispenser in a particular location based on the generated SDC algorithm. The instructions can be displayed on the substance dispenser display 220 or played as a voice message on the speakers 240 of the substance dispenser 120A/B/C.

Figure 6:
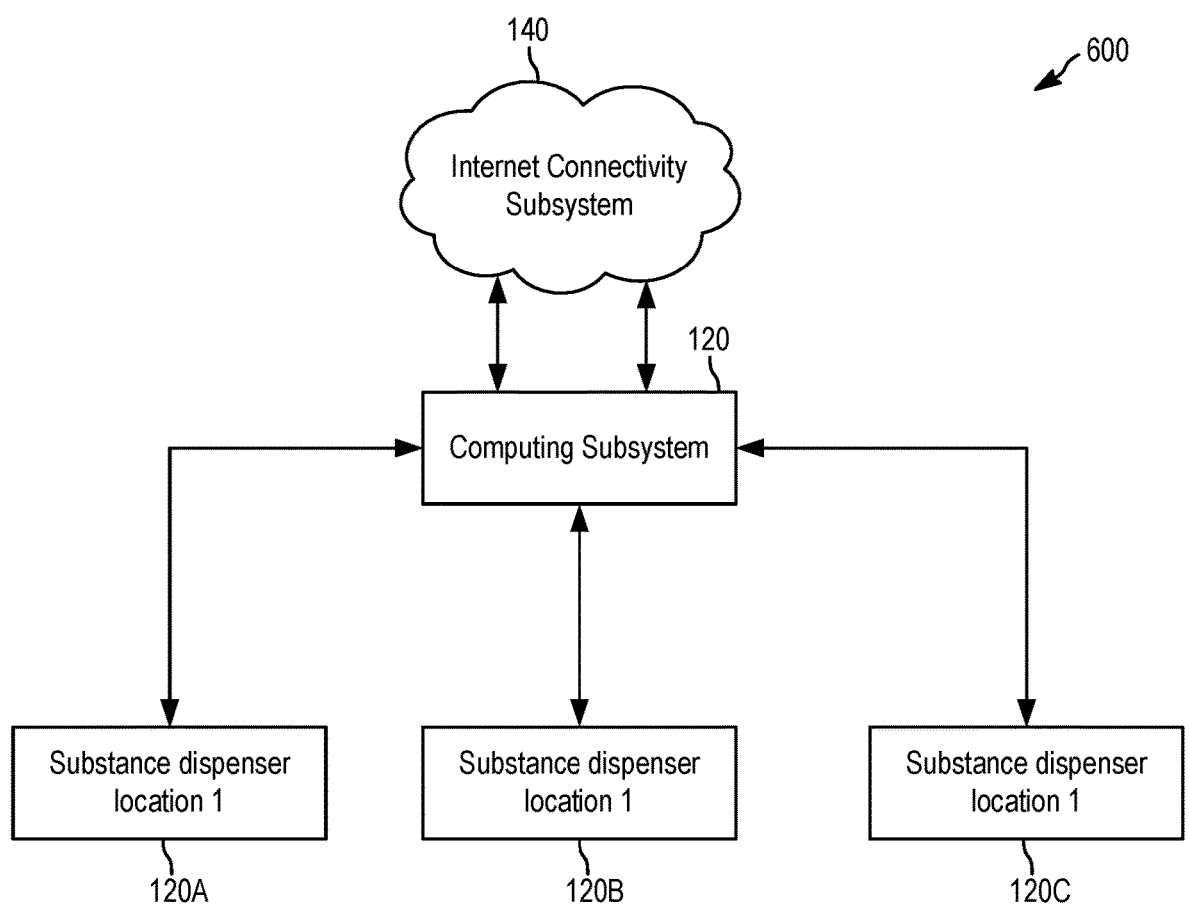
FIG. 6 illustrates a flow chart of operation of substance cessation management system.

In a preferred embodiment, referring to FIG. 6, FIG. 6 describes a system 700 for one or more substance dispensers. The computing subsystem 120 communicates with the substance packet dispenser at location 1-120A, substance packet dispenser at location 2-120B and substance packet dispenser at location 3-120C via the internet connectivity subsystem 140 to load substance packet dispensing instructions to the substance packet dispensers at the various locations based on user given details. The internet connectivity subsystem 140 leverages different technologies, to determine the substance packet dispenser proximate to the user at a given time and location, including GPS connectivity and Bluetooth technology.

Figure 7:
FIG. 7 illustrates an exemplary screen shot of display device.

The success of the SDC management is completely dependent on the commitment of the user 108 to adhere to the SDC plan and to strictly follow all the instructions. In an exemplary embodiment, a substance dependence cessation management app loaded on a mobile computing device 113, shows a screen shot 700 as shown in FIG. 7, for a "promise" by the user that he/she will only use substance packets dispensed by the substance dispenser controlled by the computing subsystem's SDC work plan and algorithm.

Figure 8:
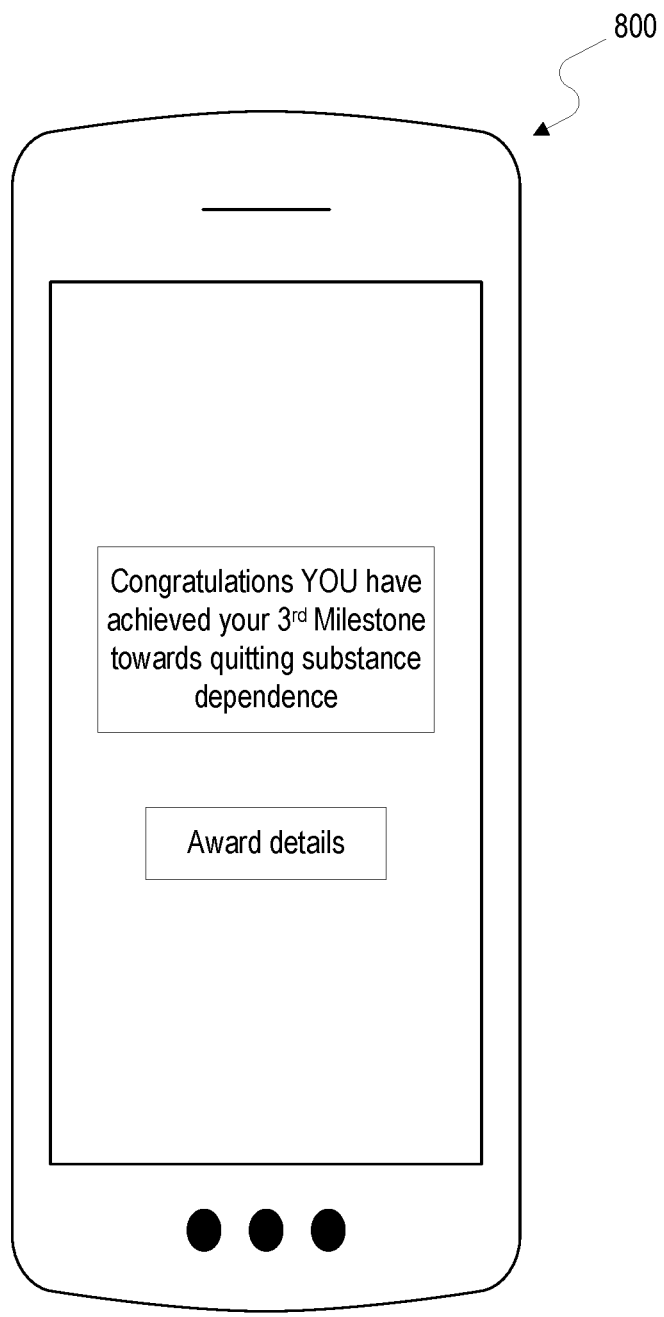
FIG. 8 illustrates an exemplary screen shot of display device.

During the duration of the SDC management program, the user 108 will be reinforced through constant encouragement by offering reward points on completion of milestones. And also educating the user with the "amount of money saved" and "length of days expected to be added to life expectancy" due to substance dependence cessation. In an exemplary embodiment, a substance dependence management software loaded on a mobile communication device 113, shows a screen shot 800 as shown in FIG. 8, for congratulating the user for achieving his part goals and by displaying "Congratulations, you have achieved your $3^{rd}$ milestone towards quitting substance dependence" and messages like "click below to see your awards".

Figure 9:
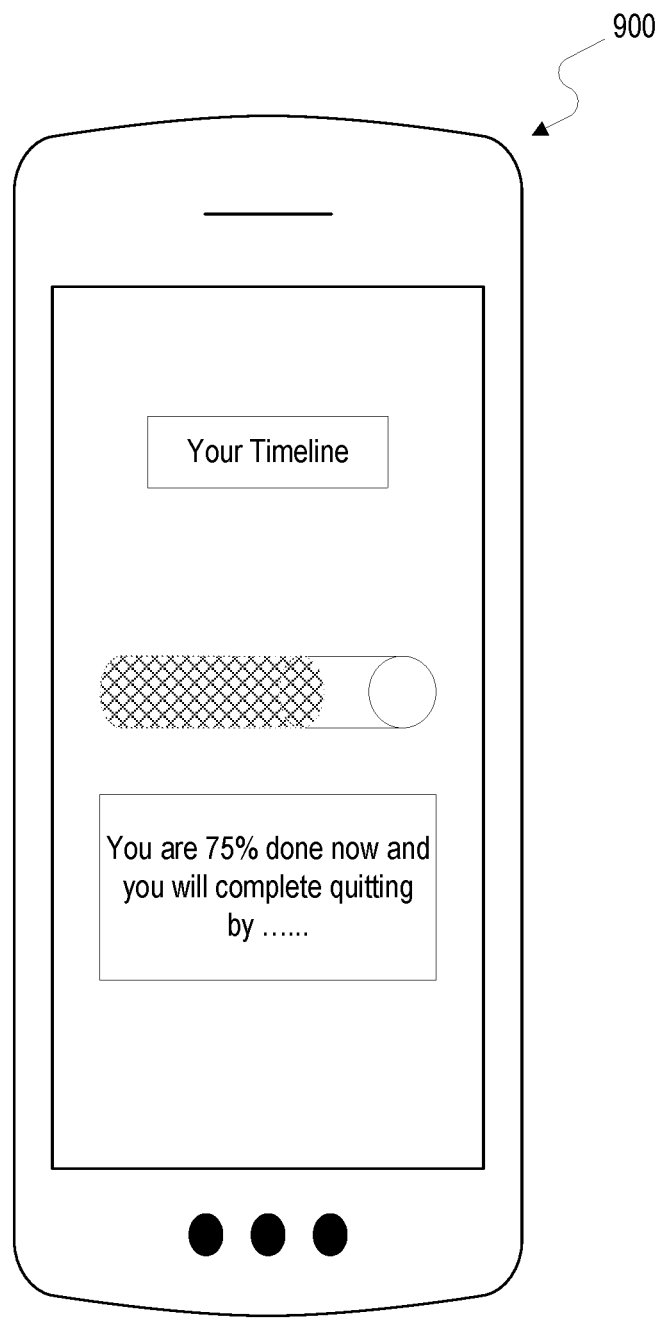
FIG. 9 illustrates an exemplary screen shot of display device.

The user 108 is provided by different options by the SDC app to check the status of the SDC plan he/she is involved. In an exemplary embodiment, a substance dependence cessation management software loaded on a mobile communicating device 113, shows a screen shot 900 as shown in FIG. 9, for displaying a timeline for substance dependence cessation and giving specific details of when SDC plan would be completed.

Figure 10:
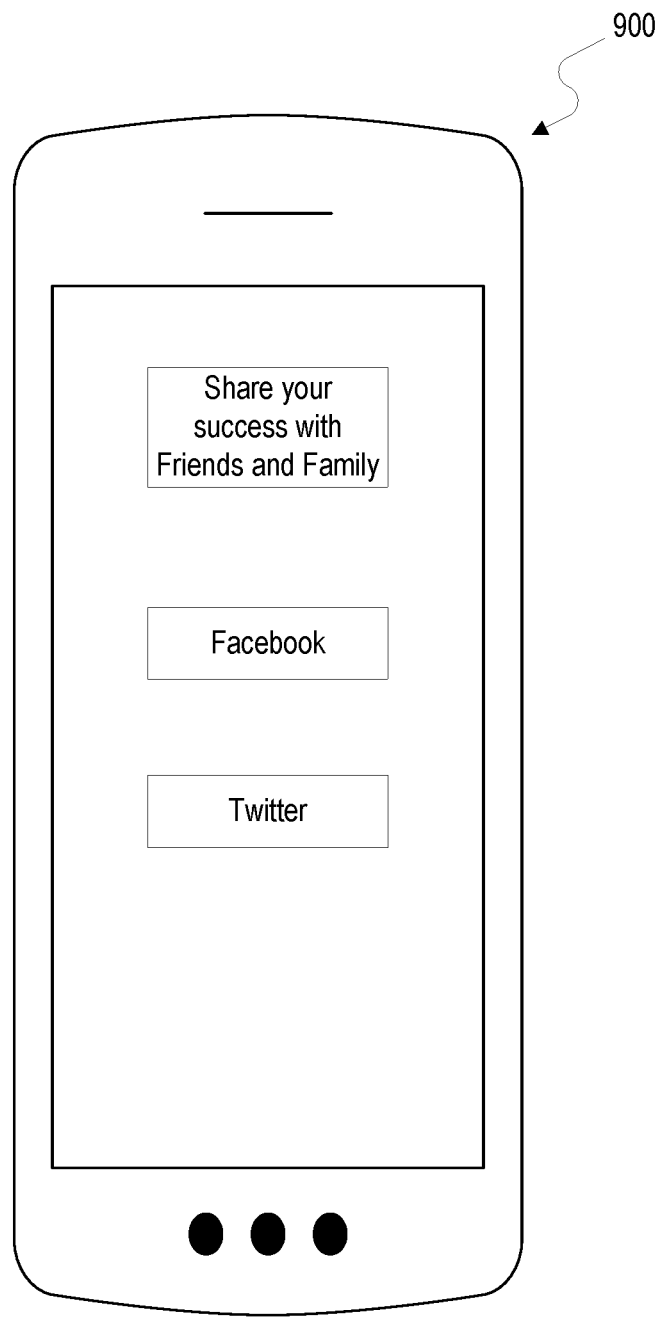
FIG. 10 illustrates an exemplary screen shot of display device.

The user 108 is provided with sharing capabilities with different social media sites through the user's mobile communication device 113 via the internet connectivity subsystem 120. In an exemplary embodiment, a substance dependence cessation management software loaded on a mobile phone, shows a screen shot 1000 as shown in FIG. 10, for sharing the success stories with friends and family through social media sites like Facebook, Twitter etc.

Figure 11:
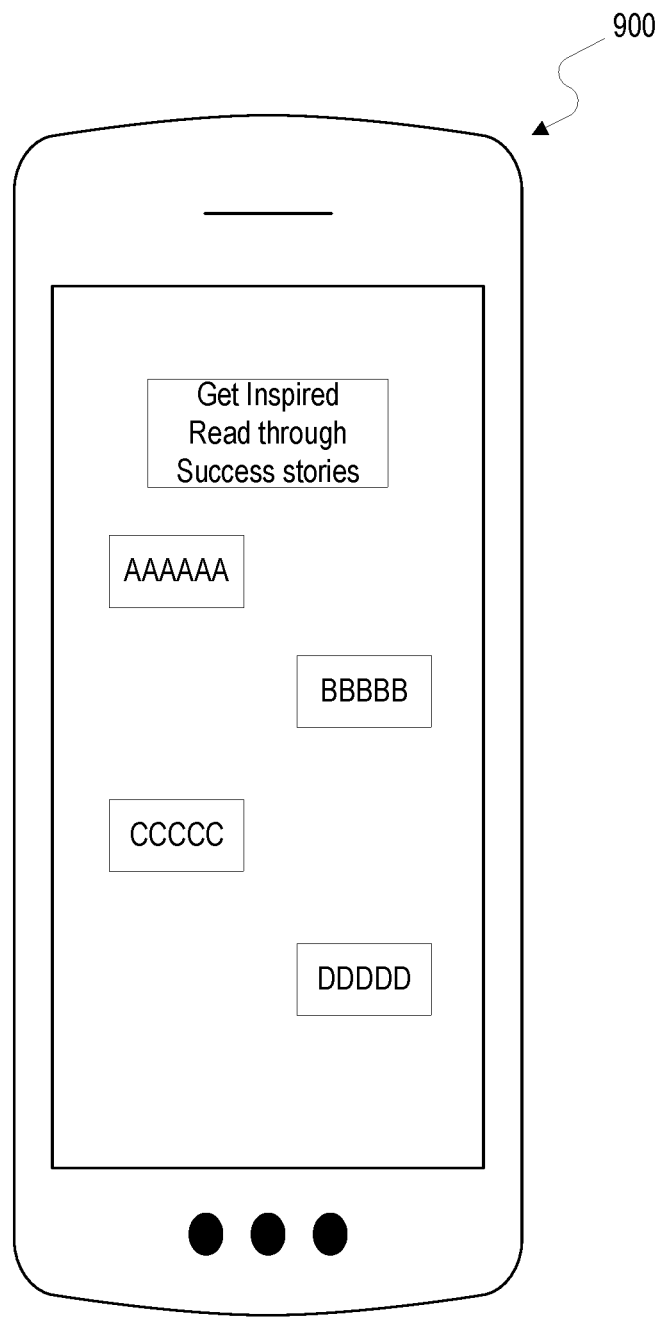
FIG. 11 illustrates an exemplary screen shot of display device.

As the user 108 is registered to the SDC management program through his/her mobile communication device 113, the user is automatically connected to the network of other users and is provided with options to read other's success stories. In an exemplary embodiment, a substance dependence cessation management software loaded on a mobile phone, shows a screen shot 1100 as shown in FIG. 11, for displaying a window to read and get inspired from other successful stories.

Figure 12:
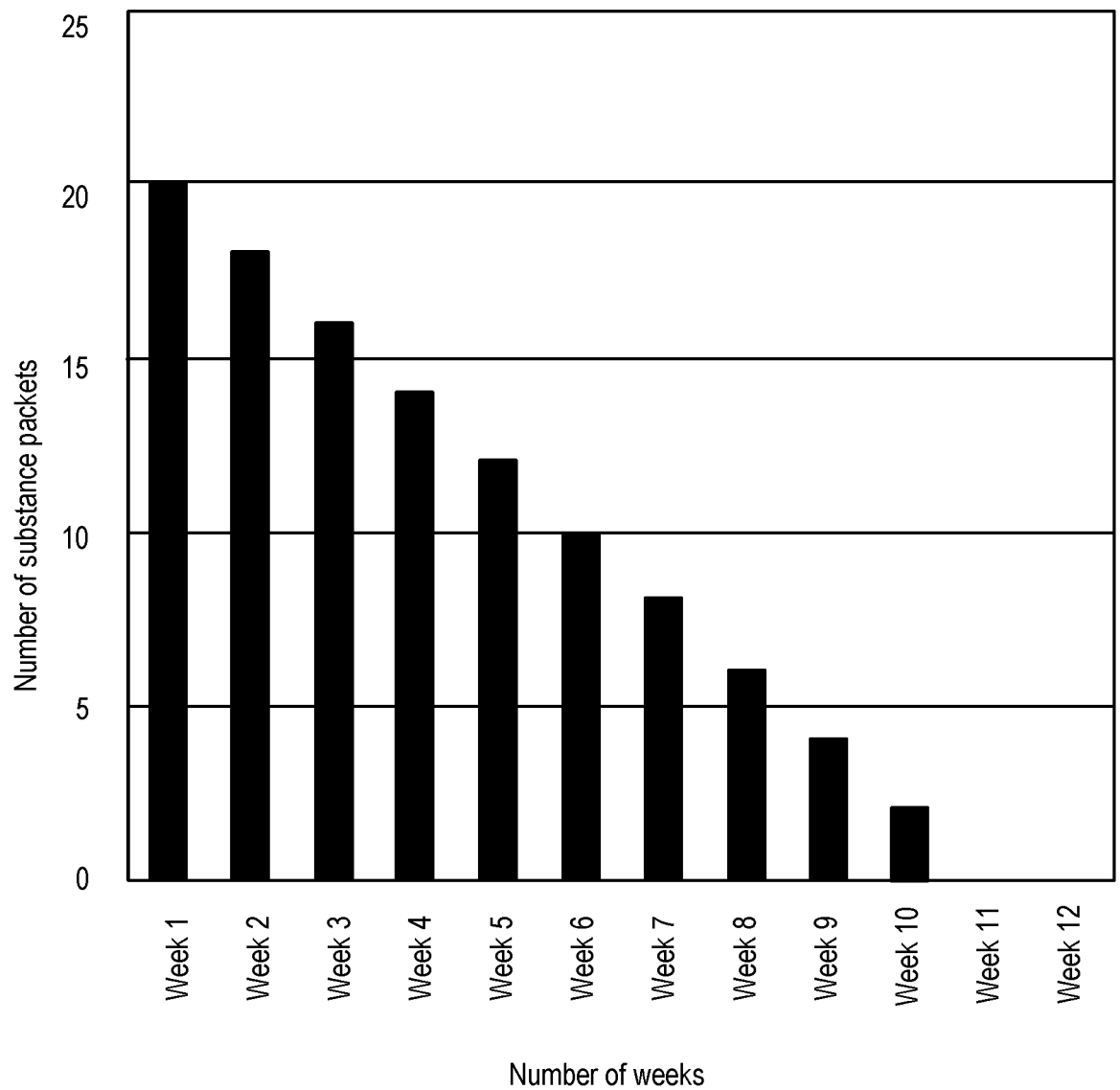
FIG. 12 is a graphical representation of a substance dependence cessation plan.

In some embodiments of the SDC management program, the rate of number of substance packets reduction includes, but not limited to, a linear reduction, a logarithmic reduction, a stepped reduction, or a combination thereof, wherein the rate of number of substance packets reduction is measured in percentage of number of substance packets per time period as illustrated by an exemplary graph in FIG. 12.

Figure 13:
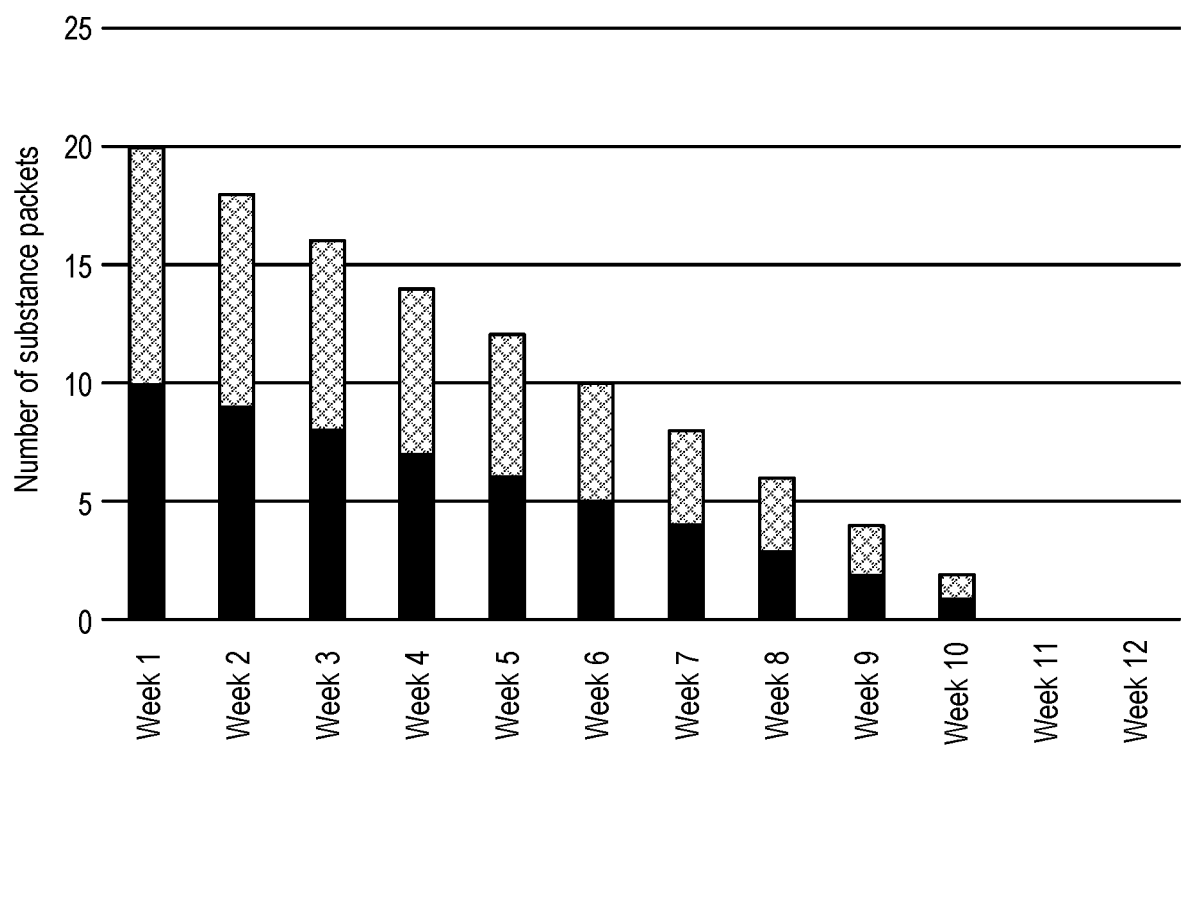
FIG. 13 is a graphical representation of a substance dependence cessation plan.

In a non-limiting embodiment, for SDC management involving nicotine-based cigarettes, nicotine-free cigarettes may be used in part of the usual number of cigarettes used per day, thereby reducing the number of nicotine-based cigarettes used per day. Many of these herbal supplements are considered harmless or even healthy when consumed. So, they form a safe and healthy substitute for nicotine-based cigarettes. The rate at which the number of cigarettes or substance packets are dispensed may be controlled and changed periodically. The rate at which the cigarettes are dispensed may be linearly reduced. In various embodiments, the rate at which the cigarettes are dispensed may be logarithmically reduced, or step function reduced. The rate of number of cigarette reduction is measured in percentage of number of cigarettes and the number of nicotine-based cigarettes per time period as illustrated by the graph in FIG. 13.

Figure 14:
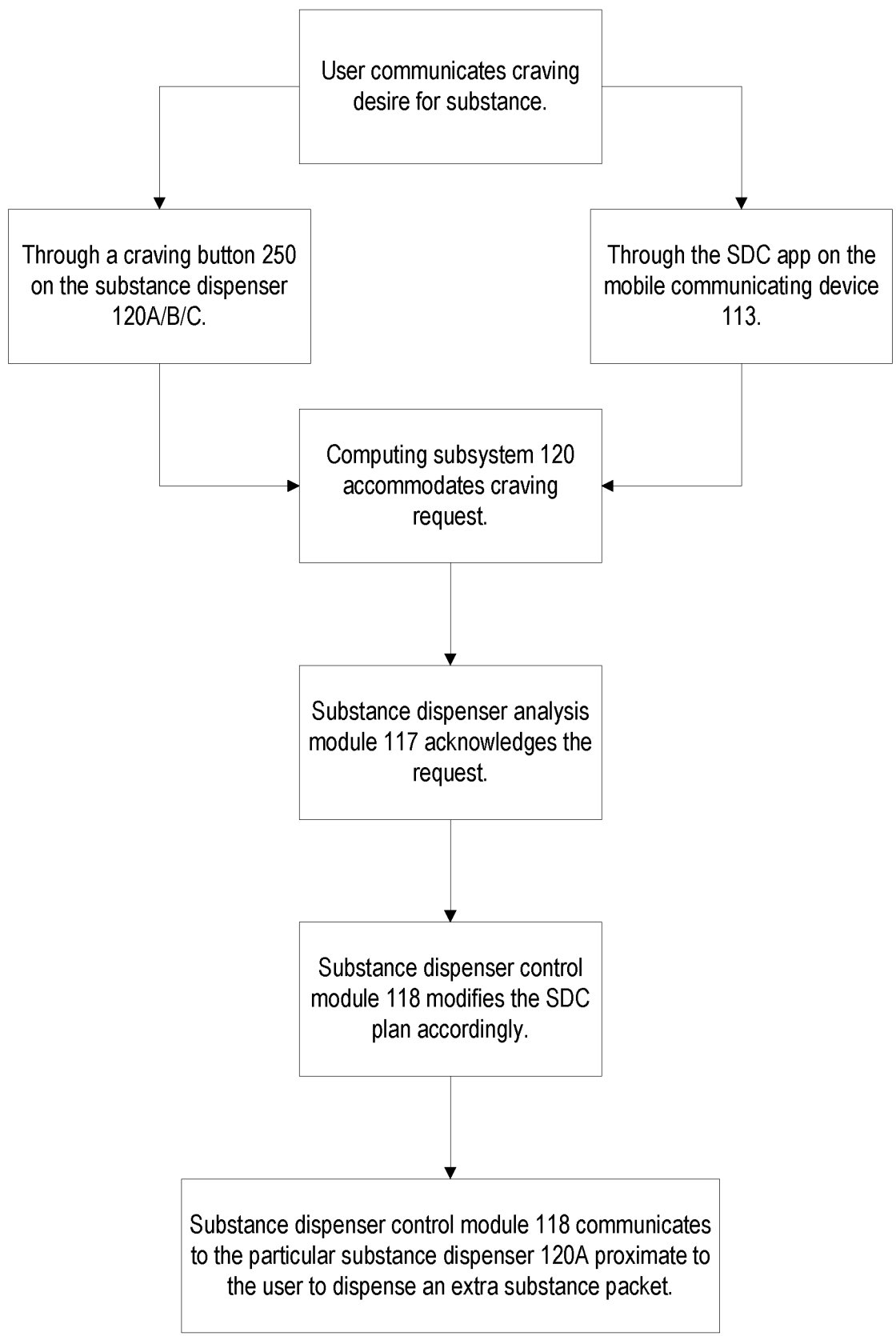
FIG. 14 illustrates flow chart for accommodating a craving request.

In some embodiments, the substance packet dispenser includes a craving button 250, where the user can press the button to get an extra substance packet apart from the usual number substance packet in the SDC plan. As it has been clinically proven that by satisfying a craving, there is more probability for the user to return back to his SDC plan and continue it further than restraining the user from satisfying his craving. Referring to FIG. 14, FIG. 14 illustrates a flow chart 1400 for the executional sequence for the SDC plan accommodating the craving desire. Initially at step 1410, the user 108 communicates the craving desire. The communication can be by pressing the craving button 250 on the substance dispenser (step—1420A) or by communicating through the SDC app (step—1420B) on the user's mobile communication device 113. At step 1430, the communication sent by the user is received by the computing subsystem 120. Further at step 1440, the computing subsystem 120 coordinates with the substance dispenser analysis module 117 to accommodate the craving request by the user in the SDC algorithm and SDC work plan. A modified SDC algorithm and SDC work plan is generated including the addition craving satisfying substance packet. At step 1450, the modified SDC plan is communicated to the substance dispenser control module. Finally, at step 1460, the substance dispenser control module communicates the modified SDC plan to the substance dispenser closely proximate to the user 108 to dispense a substance packet immediately to satisfy the craving desire of user.

Figure 15:
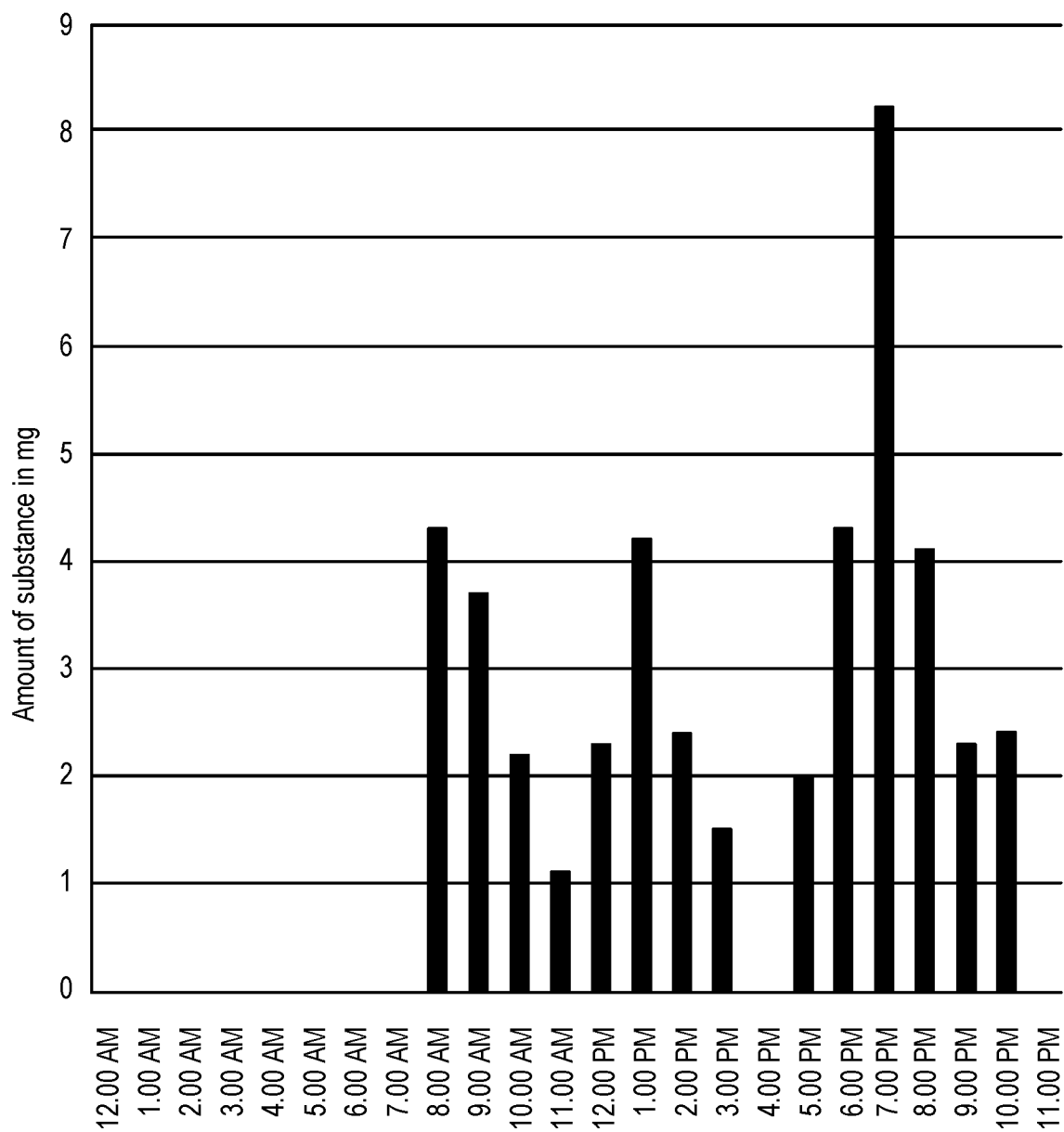
FIG. 15 is a graphical representation of a substance dependence cessation plan.
Figure 16:
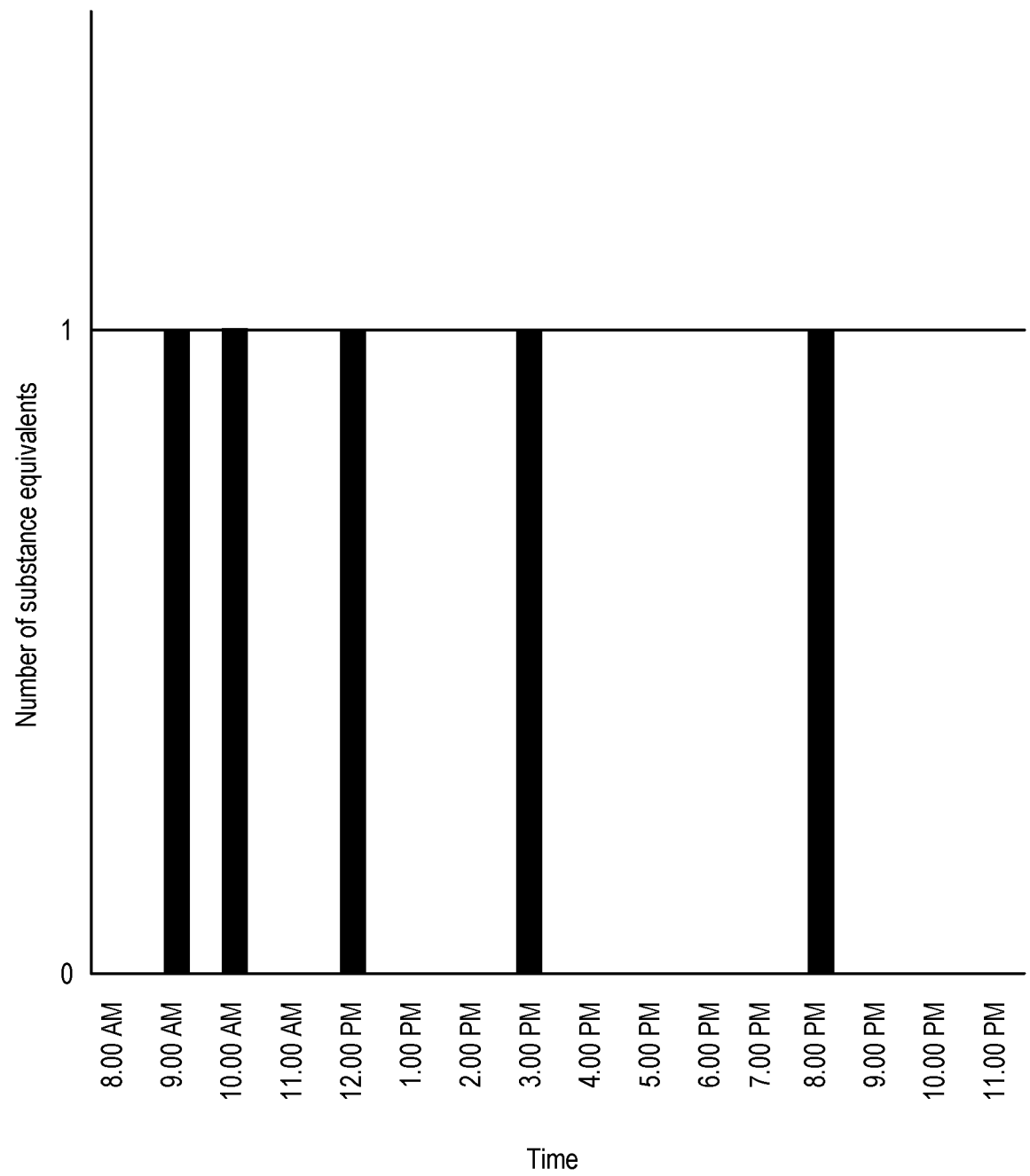
FIG. 16 is a graphical representation of a substance dependence cessation plan.

FIGS. 15 & 16 illustrate graphic outputs showing the user's daily frequency data output for substance packet intake and a user's daily inter-substance packet spacing data for an exemplary SDC management protocols. These represent exemplary data that is stored in the data storage 119 of the computing subsystem 120 and which can be further shared with the user and or a clinical professional.

In some embodiments of the substance dispenser 120A/B/C, the electronic communication system for communicating with one or more other electronic device comprises: a wireless internet connectivity subsystem 140; and a wired communication link, wherein the other electronic device comprises: a computer, a mobile device, a computer network, and an electronic storage data device, as illustrated in.

In some embodiments, a substance cessation method uses one to multiple substance dispenser apparatus 120 that can hold multiple substance packets in a chamber. When an user 108 is ready to quit substance dependence, the method uses an iOS and Android app to enter various details prior to starting a program. Data required prior to initiation includes but not limited to Name, DOB, Duration of substance dependence, number of substance packets consumed on average/day, wake up time, bed time, places where substance packets consumed, home, office, car, physical location where substance packets are purchased, how much money spent on substance packets per week. After the appropriate data is entered, the method activates an algorithm and instructs the individual to load the number of substance packets as recommended. The Algorithm will also recommend the approximate number of devices required and number of substance packets required to be loaded in each device. In some embodiments, the algorithm will calculate and start dispensing substance packets at calculated times and increasing the duration every day by few min (duration generated by algorithm). If an individual has more than one devices, substance packet is only dispensed by the closest device as calculated by the Bluetooth connectivity by the smart device running the App. If a substance packet is dispensed by one device, it won't be dispensed by the other device as per the communication among all devices thus creating a mesh network forming a backbone for the algorithm.

Alternative SDC management plans are contemplated herein. For non-limiting example, a SDC management plan may comprise a fast rate tapering, which reduces the consumption of substance packets used by a user from their current usage profile to zero substance dependence in a week, in two weeks, in three weeks, in four weeks, in five weeks, in six weeks, in seven weeks, in up to eight weeks. For non-limiting example, a SDC management plan may comprise a medium rate tapering which reduces a user's substance dependence from their current usage profile to zero substance dependence in two months, in eight weeks, in nine weeks, in ten weeks, in eleven weeks, in up to twelve weeks, or in two months to three months. For non-limiting example, a management plan may comprise a slow rate tapering which reduces the consumption of substance packets used by a user from their current usage profile to zero substance dependence in three months, in twelve weeks, in thirteen weeks, in fourteen weeks, in fifteen weeks, in sixteen weeks, in seventeen weeks, in eighteen weeks, in three months to six months, in three months to four months, in three months to five months, or in up to six months. For non-limiting example, a management plan may comprise an extra slow rate tapering which reduces the consumption of substance packets used by a user from their current usage profile to zero substance dependence in over six months, in twenty-six to 52 weeks, or six months to one year, or up to one year. Longer plans may be used, or shorter plans or a combination of longer and shorter plans may alternatively be used based on the user 108 response to any of the substance cessation plan.

In some embodiments, two or more substance dependence management systems can be tagged to each other by locating them through Bluetooth beacons for micro location awareness. Once the two or more substance dependence management systems are tagged they can pair automatically for data sharing. The locational details corresponding to latitudinal and longitudinal coordinates for the two or more-substance dependence management system. The coordinates in addition to address are stored associated with each session In some embodiments, facial recognition can be used for a password to tag sessions based off of a photograph with the responsible party for dispensing substance packets from a substance dispenser. This uses the front facing camera of the mobile computing device 113 of the user sub system 110.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system, or a printer circuit board. Embodiments within the scope of the present disclosure include program products comprising machine readable media for carrying or having machine-executable instructions or data structures stored thereon. Such machine-readable media can be any available media that can be accessed by a general purpose or special purpose computer or another machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or another machine with a processor. When information is transferred, or provided over a network or another communications connection (either hardwired, wireless, or a combination of hardwired or wireless) to a machine, the machine properly views the connection as a machine-readable medium. Thus, any such connection is properly termed a machine readable medium. Combinations of the above are also included within the scope of machine-readable media. Machine-executable instructions include, for example, instructions and data which cause a general-purpose computer, special purpose computer, or special purpose processing machines to perform a certain function or group of functions.

Although the figures may show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps and decision steps.

The instant invention may be embodied in other forms or carried out in other ways without departing from the spirit or essential characteristics thereof. The present disclosure is therefore to be considered as in all respects illustrative and not restrictive, the scope of the invention being indicated by the appended claims, and all equivalency are intended to be embraced therein. One of ordinary skill in the art would be able to recognize equivalent embodiments of the instant invention and be able to practice such embodiments using the teaching of the instant disclosure and only routine experimentation.

The invention claimed is:

1. A system for substance dependence cessation management, comprising:
   an electronic mobile device;
   a communication network; and
   a substance packet dispenser connected to the electronic mobile device through the communication network,
   the substance packet dispenser is configured to dispense packets based on a substance dependence cessation (SDC) plan that is generated based on personal information, comprising dependence on a substance, of a user;
   wherein the system is adapted to reward the user for adhering to a number of substance packets dispensed by the substance packet dispenser.

2. The system of claim 1, wherein the system is adapted to control dispensing of one or more substance packets from the substance packet dispenser.

3. The system of claim 1, wherein the system is adapted to collect user information relating to the user.

4. The system of claim 3, wherein the system is adapted to activate an algorithm on the electronic mobile device based on the user information and define a plan of cessation of substance dependence.

5. The system of claim 1, wherein the system is adapted to identify a substance packet dispenser proximate to the user for dispensing substance packets at scheduled times.

6. The system of claim 1, wherein the system is adapted to ensure substance packets are dispensed only at a single dispenser at a given timeframe.

7. The system of claim 1, wherein the substance packet dispenser comprises:
   a chamber for holding one or more substance packets, embedded with a sensor to determine the number of substance packets in the chamber;
   a display for displaying the number of substance packets in the chamber; and
   a dispensing outlet through which the substance packets are dispensed.

8. The system of claim 7, wherein the system is adapted to control an opening and closing of the chamber for loading substance packets.

9. The system of claim 7, wherein the substance packet dispenser comprises a pair of speakers adapted to play a message to the user.

10. The system of claim 7, wherein the substance packet dispenser is equipped with a craving button which can be used to indicate a craving feeling of the user.

11. The system of claim 10, wherein the system is configured to modify the SDC plan based on execution of the craving button.

12. The system of claim 1, wherein the SDC plan is based on a proximity of substance usage locations to the user at time intervals through a day.

13. The system of claim 12, further comprising one or more additional substance packet dispensers connected to the electronic mobile device through the communication network.

14. A method for substance dependence cessation management, comprising:
    registering a user for substance dependence cessation management;
    collecting substance dependence information relating to the user;

saving the substance dependence information relating to the user;

generating a substance dependence cessation plan, based on personal information, comprising dependence on a substance, for the user; and rewarding the user for adhering to the substance dependence cessation plan based on a number of substance packets that are dispensed by a substance packet dispenser.

15. The method of claim 14, further comprising providing instructions to the user regarding a number of substance packets to be loaded into the substance packet dispenser.

16. The method of claim 14, further comprising controlling a number of substance packets dispensed from the substance packet dispenser to the user at a given time frame.

17. The method of claim 14, further comprising estimating a time for substance dependence cessation completion and providing one or more details regarding the estimated time to the user.

18. The method of claim 14, further comprising sharing one or more success stories with friends and family through social media connections.

19. The method of claim 14, further comprising dispensing an extra substance packet apart from a usual number of substance packets in response to the user indicating a craving feeling.

20. A substance dispenser apparatus for substance dependence cessation management, comprising:

a chamber for holding substance packets; and a dispensing outlet through which the substance packets are dispensed, wherein the substance dispenser apparatus is capable of being controlled by a software program to dispense a particular number of substance packets at a specific time that is based on personal information of a user, the personal information comprising dependence on a substance, and wherein the software program is adapted to reward the user for adhering to the particular number of substance packets dispensed by the substance dispenser apparatus.

* * * * *